United States Patent [19]

Pope, Jr.

[11] 4,278,084
[45] Jul. 14, 1981

[54] NON AIR-BLOCKING FILTER

[75] Inventor: J. Lee Pope, Jr., Baltimore, Md.

[73] Assignee: Baxter Travenol Laboratories, Inc., Deerfield, Ill.

[21] Appl. No.: 86,462

[22] Filed: Oct. 19, 1979

[51] Int. Cl.³ .............................................. A61M 5/16
[52] U.S. Cl. .............................. 128/214 R; 128/214C; 55/159; 210/927
[58] Field of Search ................ 128/214, 214 C, 214.2; 55/158, 159; 210/94, DIG. 23

[56] References Cited

U.S. PATENT DOCUMENTS

| | | | |
|---|---|---|---|
| 3,803,810 | 4/1974 | Rosenberg | 55/159 |
| 4,004,587 | 1/1977 | Jess | 128/214 |
| 4,009,714 | 3/1977 | Hammer | 128/214 C L |
| 4,116,646 | 9/1978 | Edwards | 128/214 R X |
| 4,190,426 | 2/1980 | Ruschke | 55/159 X |
| 4,200,095 | 4/1980 | Reti | 128/214 C |

Primary Examiner—Stephen C. Pellegrino
Attorney, Agent, or Firm—Paul C. Flattery; John P. Kirby, Jr.; Gary W. McFarron

[57] ABSTRACT

A filter assembly is disclosed for use, in-line, in a medical fluid, e.g., parenteral solution, administration set or the like, to filter the fluid as it is administered to a patient. Hydrophobic and hydrophilic filter membranes are mounted in a parallel-flow relationship within a filter housing, which is sealed except for inlet and outlet ports. The membranes are respectively positioned so that the hydrophobic filter membrane is located above the hydrophilic filter membrane when the filter assembly is suspended in-line in an administration set, permitting any air separated from the fluid by the hydrophilic membrane to migrate upwardly and pass through the hydrophobic membrane instead of accumulating on the surface of and blocking flow through the hydrophilic membrane.

4 Claims, 4 Drawing Figures

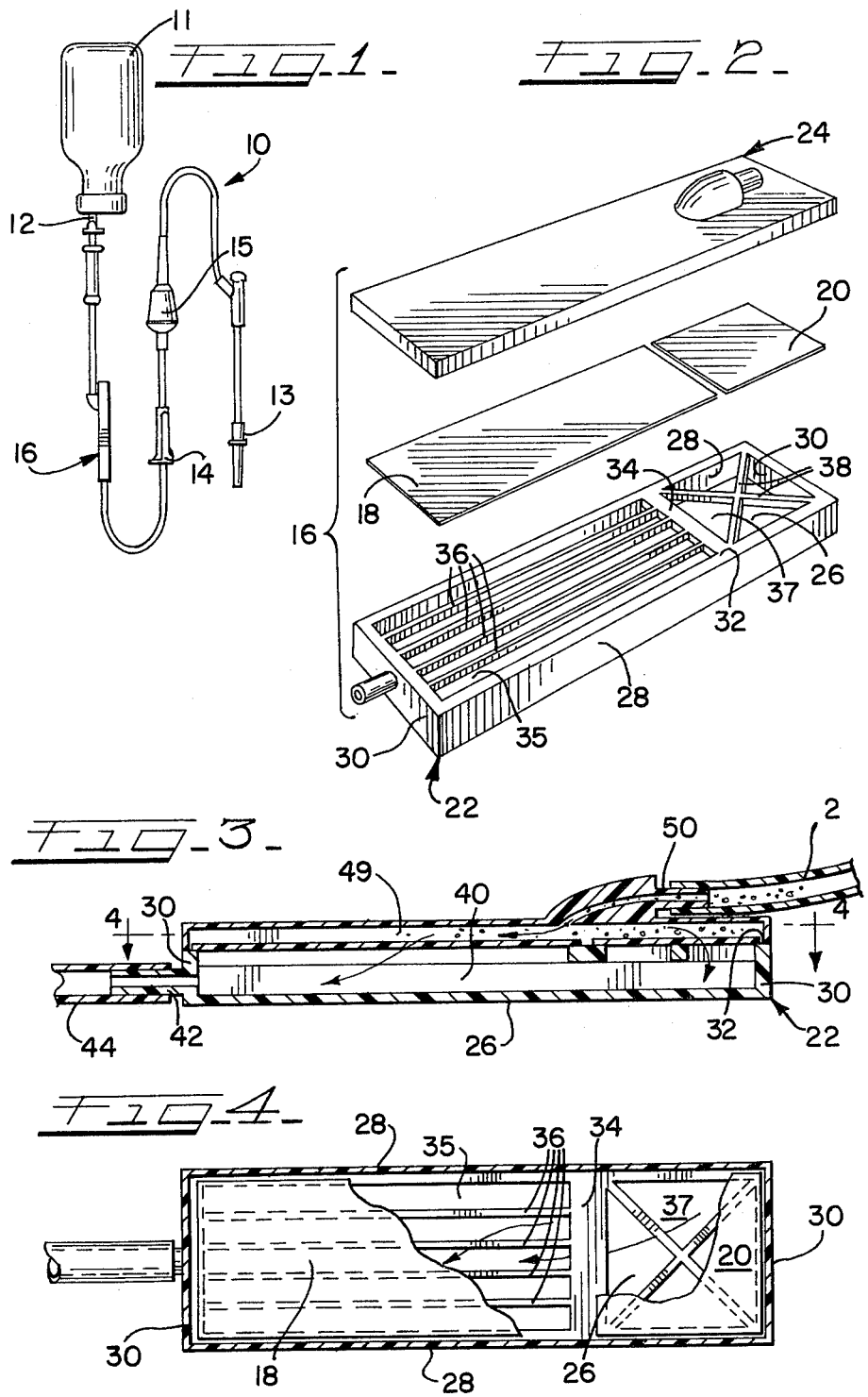

NON AIR-BLOCKING FILTER

The present invention relates generally to filters, and more specifically to medical fluid filters adapted to provide microporous filtration of parenteral solutions or the like as they are administered to a patient.

There is a growing interest in the medical field in providing for filtration of intravenous fluids, for example, parenteral solutions, as they are administered to the patient, to remove microscopic particulate. Many of the current filter devices achieve such filtration by directing the solution through a microporous membrane, which may have a pore size of less than one micron. These membranes, however, are usually "hydrophilic" in nature, which means that once wetted by the filtering liquid, the membranes are substantially impervious to small gas or air bubbles which may be entrained in the liquid. When this happens, air bubbles may accumulate on the surface of the hydrophilic filter membrane until they impair, or completely block the passage of liquid through the filter. This is a phenomenon often referred to as "air blocking," and requires periodic monitoring by medical personnel to see that the flow of liquid is not impaired.

One solution to air-blocking has been to provide a hydrophobic filter membrane in the flow passageway, which by the nature of the material, is permeable to gas but impermeable to liquid, thus allowing the small bubbles to pass downstream with the liquid. For example, it has been suggested in U.S. Pat. No. 3,520,416 to Keedwell to use a microporous filter material which is hydrophilic in some areas, and hydrophobic, as by the application of silicone treatment, in other areas. In addition to other shortcomings, this material is relatively expensive, it does not permit the use of different pore sizes for the hydrophobic and hydrophilic filters, and the relative proportion of the hydrophobic and hydrophilic filter areas is difficult to precisely maintain.

Other filters have employed a separate hydrophobic filter membrane to vent any gas separate from the fluid stream to the atmosphere. Compare, for example, U.S. Pat. Nos. 3,803,310 and 3,523,408, both to Resenberg. With these filters, however, the filtering solution would be exposed to the ambient atmosphere if the hydrophobic membrane failed or was accidentally punctured.

One successful design, which does not have any possibility of exposing the liquid to the ambient atmosphere and which does not air-block, is illustrated in U.S. Pat. No. 4,004,587 to Jess. The filter device there, which is sold as the "MP-5" by Travenol Laboratories, Inc., of Deerfield, Ill., uses a pair of facing hydrophobic and hydrophilic membranes in parallel flow relationship within a sealed housing through which the liquid and gas passes. Such a filter does not prevent small gas bubbles from passing downsteam, but rather provides a final filtration for the medical fluid without the problem of air-blocking.

Although the filter shown in the '587 patent to Jess works well and has been readily accepted by the medical profession, because of the size and structure, it also involves a relatively complex and time consuming manufacturing technique.

Accordingly, it is a general object of the present invention to provide a non air-blocking filter which is relatively easy to manufacture at low cost.

It is a further object of the present invention to provide a non air-blocking filter which may be included as part of a fluid administration set.

It is a still further object of the present invention to provide a non air-blocking filter that does not require special monitoring or care by the medical staff when it is used.

These and other objects of the present invention are set forth in the following detailed description of the preferred embodiment of the present invention, as shown in the attached drawings, of which:

FIG. 1 is a plan view of a medical fluid administration set for parenteral fluids and the like, including an in-line filter made in accordance with the present invention.

FIG. 2 is an exploded view of a filter assembly embodying the present invention.

FIG. 3 is a vertical sectional view of the FIG. 2 filter assembly taken along its longitudinal axis.

FIG. 4 is a sectional view, with part of the filter membrane removed, taken along line 4—4 of FIG. 3.

The present invention is generally embodied in administration set 10 for administering medical fluid, for example parenteral solution, from an elevated reservoir 11 to a patient. One end of the administration set typically includes a spike 12 for insertion, through an access membrane, into the fluid reservoir. The other end of the set terminates with a needle hub or luer connector 13, for securing the set to a needle or catheter attached to the patient. A typical administration set may also include a flow control clamp 14 and one or more medication addition sites 15. In accordance with the present invention, a non air-blocking filter, generally at 16, is secured in-line in the administration set to provide microporous filtration of the fluid as it is administered to the patient. To prevent air-blocking as well as to permit simple priming of the administration set, the filter 16 includes a hydrophilic filter membrane 18 and a hydrophobic membrane 20 in a parallel flow combination, so that each element of fluid passing into the filter passes through one or the other hydrophobic or hydrophilic membranes, and the membranes are relatively positioned so that when the administration set is suspended from an elevated fluid reservoir, the hydrophobic membrane is above the hydrophilic membrane, allowing any air bubbles separated from the liquid by the hydrophilic membrane to rise upwardly and pass through the hydrophobic membrane rather than accummulating on the surface of the hydrophilic membrane until it air blocks. Except for inlet and outlet openings, the filter 16 is sealed from the ambient atmosphere, so there is no possibility of exposing the filtering solution to atmospheric bacteria or the like.

Turning now to a more detailed description of the preferred embodiment of the present invention, the filter 16 is generally elongated in shape, with a two-part plastic housing made up of a base portion 22 and a cap portion 24, both made of rigid plastic or similar material. The base portion 22 has bottom wall 26, joined with side walls 28, end walls 30, and an open, grid-forming top wall 32 that provides a flat support surface and grid structure for the hydrophobic an hydrophilic membranes 18 and 20.

The open top wall 32 of the base portion 22 has a cross member, at 34, dividing the open wall into a pair of openings 35 and 37 which are spaced apart in the longitudinal direction of the base portion 22 and are covered by the filter membranes 18 and 20, respectively, through which any liquid and gas passes. The openings 35 and 37 are of different size, with the larger opening 35 provided for the filtering liquid, and including a series of parallel underlying support ribs 36 to support and reinforce the hydrophilic membrane 18 mounted on the supporting wall 32. The smaller opening 37, which is covered by the hydrophobic membrane 20 and through which any entrained gas passes, has a pair of underlying, crossing support ribs 38 to support the membrane 20. As best seen in FIG. 3, the support wall 32 is spaced from the bottom wall 26 of the base portion 22, to define an outlet chamber 40 where any gas or liquid passing through the filter is recombined for passage downstream through an outlet port 42 in the lower end wall 30, which is attached to plastic tubing 44 of the administration set.

The hydrophobic and hydrophilic membranes 18 and 20 are separate pieces, and the pore size and material may be selected, depending on circumstances such as the fluid to be filtered, and the flow rate and degree of filtration desired. For example, the hydrophilic membrane may be of a variety of materials, such as polyester, polyvinylchloride or the like. One typical hydrophilic filter is a cellulose membrane having a mean pore size of about 0.22 microns, which is small enough to remove even bacteria. Such a filter membrane is commercially available from Millipore Corporation of Bedford, Mass. Of course, the pore size may be varied, but preferably it is sufficiently small to remove at least 90 percent of all particles 5 microns or larger. The peripheral edge of the hydrophilic membrane 18 may be sealed to the top support 32 of the base 22 in a variety of ways, including without limitation, direct heat sealing, solvent bonding, or by clamping the membrane between the top wall 32 of the base portion and the lower edge of the cap portion 24.

The hydrophobic membrane 20 may also be selected from a wide variety of materials and pore sizes. For example a silicone-treated membrane may be used as the hydrophobic membrane, but the preferred material is polytetrafluroethylene, better know as Teflon plastic, which is naturally waterrepellent and gas permeable. The pore size of the hydrophobic membrane may vary but is typically between about 1.5 and 3 microns. A material that has been successfully used as hydrophobic material is medical fluid filters if type L10931 from the Gore-tex Elkton, Md. The peripheral edge of this hydrophobic membrane is attached to the peripheral support surface 32, as, e.g., by solvent bonding, a heat-seal type attachment or clamping between the support surface 32 the filter cap 24. As noted before, the hydrophilic membrane 18 is much larger, at least about twice as large, as the hydrophobic membrane 20, since the amount of air or gas entrained in the medical liquid is extremely small relative to the amount of liquid.

The filter membranes 18 and 20 are covered and enclosed by the shallow cap 24, which is peripherally welded or bonded to the base portion 22 of the housing and defines an inlet chamber 49 between the inside surface of the cap and the filter membranes. The cap includes an inlet opening port 50 in the top wall 46 which is pointed upwardly for attachment to another section of plastic tubing 52 of the administration set. Of course, the inlet opening could also be in the end wall of the cap, but in any event, it is preferably positioned generally opposite the outlet port 42 in the base portion 22, so that when suspended in a fluid administration set, the filter hangs so that the filter membranes 18 and 20 are generally vertical, with the hydrophobic membrane 18 above the hydrophilic membrane 20. As fluid enters the inlet chamber 49 defined between the filters 18 and 20 and the inside surface of the cap, the liquid portion passes through the hydrophilic membrane 18, into the outlet chamber 40 and through the outlet port 42 to the patient. Whenever any entrained gas or air bubbles engage the hydrophilic filter, they are separated from the liquid and, by their natural buoyancy float upwardly to adjacent the hydrophobic membrane 20. When sufficient gas accumulates to contact the hydrophobic membrane, the gas passes through the membrane and into the outlet chamber 40 where it mixes with the liquid passing through the hydrophilic membrane 18 and then continues through the outlet port 42.

In operation, an administration set is usually primed to expel air and fill it with liquid before it is attached to a patient. During priming, the filter of the present invention is simply inverted so that gas in the inlet chamber 49 filter passes through the hydrophilic filter before it becomes wetted, and is expelled downstream through the outlet port 42. After priming, the filter is permitted to hang in the normal attitude so that any entrained air in the fluid is allowed to pass through the hydrophobic membrane and does not accumulate on the surface of the hydrophilic membrane to block flow of liquid therethrough.

Although the present invention has been described in terms of the preferred embodiment, this invention, as set forth in the attached claims, is also intended to include those equivalent structures, some of which may be apparent upon reading this description, others of which may be apparent only after some study.

What is claimed is:

1. A medical fluid filter assembly adapted to be suspended substantially vertically, in-line, in a medical fluid administration set, said assembly comprising:
   an elongated housing defining an elongated chamber therewithin;
   interior wall means extending from end to end within said chamber and dividing said chamber into a pair of adjacent elongated subchambers;
   inlet opening means substantially at one end of said housing communicating with one of said subchambers;
   outlet opening means substantially at the other end of said housing and communicating with the other of said subchambers;
   said chamber being otherwise closed to the exterior;
   said wall means comprising a hydrophobic filter membrane adjacent said one end of said chamber and a hydrophilic filter membrane adjacent said other end of chamber, whereby said filter assembly is position sensitive, such that when said filter assembly is suspended vertically in an administration set, said hydrophobic membrane is located above said hydrophilic membrane to permit the passage of entrained air bubbles and prevent blockage of the hydrophilic filter.

2. A filter assembly in accordance with claim 1, wherein said housing comprises an elongated base portion, including a peripheral support surface defining a pair of vertically spaced openings therein, said hydrophobic filter membrane covering the upper one of said openings, and said hydrophilic filter membrane covering the lower one of said openings, said housing means further comprising a cap portion secured to said base portion over said membranes to cover and seal said membranes from the ambient atmosphere.

3. A filter assembly in accordance with claim 2 wherein said upper one of said spaced openings is substantially smaller than said lower one of said spaced openings.

4. A filter assembly in accordance with claim 3 wherein said base portion includes underlying support ribs spanning said each of openings to support said filter membranes.

* * * * *